(12) United States Patent  
Beute

(10) Patent No.: US 8,147,431 B2  
(45) Date of Patent: Apr. 3, 2012

(54) MEASURING MEMBER AND DEVICE FOR DETERMINING THE BLOOD FLOW OF THE GASTROINTESTINAL TRACT, AS WELL AS FOR REGISTRATING THE INTESTINAL PERISTALSIS

(75) Inventor: Jan Beute, Almere (NL)

(73) Assignee: Q-Pidt BV (NL)

( * ) Notice: Subject to any disclaimer, the term of this patent is extended or adjusted under 35 U.S.C. 154(b) by 254 days.

(21) Appl. No.: 11/814,735

(22) PCT Filed: Feb. 8, 2006

(86) PCT No.: PCT/NL2006/000065
§ 371 (c)(1),
(2), (4) Date: Mar. 24, 2008

(87) PCT Pub. No.: WO2006/088355
PCT Pub. Date: Aug. 24, 2006

(65) Prior Publication Data
US 2008/0319339 A1    Dec. 25, 2008

(30) Foreign Application Priority Data

Feb. 17, 2005   (NL) .................................. 1028320

(51) Int. Cl.
*A61B 5/103* (2006.01)
*A61B 5/117* (2006.01)
*A61B 5/02* (2006.01)
*A61B 5/00* (2006.01)

(52) U.S. Cl. .......... 600/593; 600/504; 600/561
(58) Field of Classification Search .......... 600/485, 600/486, 504, 561, 583, 587, 593
See application file for complete search history.

(56) References Cited

U.S. PATENT DOCUMENTS

| 5,865,801 | A  | * | 2/1999 | Houser .................. 604/103.07 |
| 6,071,237 | A  | * | 6/2000 | Weil et al. ................. 600/309 |
| 6,315,733 | B1 | * | 11/2001 | Zimmon .................... 600/486 |
| 2004/0171942 | A1 | * | 9/2004 | Ackerman et al. .......... 600/486 |

* cited by examiner

*Primary Examiner* — Max Hindenburg
*Assistant Examiner* — Adam Eiseman
(74) *Attorney, Agent, or Firm* — Laubscher & Laubscher, P.C.

(57) ABSTRACT

A measuring member and a device to be used for determining the blood flow of the gastrointestinal tract, includes an intestinal probe, having its distal end provided with a flexible inflatable body and at least one pressure sensor mounted on this supporting body. After bringing the inflatable flexible body to predetermined pressure, the pressure sensor will abut the intestinal wall and the measured pressure development, which represents a measure for the blood flow of the gastrointestinal tract, is transformed into a graphical image with the help of the device and/or is transformed into actual values for the blood flow of the gastrointestinal tract. Further, the measuring member measures the development of the pressure within the inflatable flexible body, which represents a measure for the intestinal peristalsis.

20 Claims, 1 Drawing Sheet

U.S. Patent     Apr. 3, 2012     US 8,147,431 B2

MEASURING MEMBER AND DEVICE FOR DETERMINING THE BLOOD FLOW OF THE GASTROINTESTINAL TRACT, AS WELL AS FOR REGISTRATING THE INTESTINAL PERISTALSIS

BACKGROUND OF THE INVENTION

The present invention relates to a measuring member allowing for measuring changes in volume of the blood present in the gastrointestinal tract, in which the measured changes in volume are a measure of the blood flow of the gastrointestinal tract and its course in time. In the medical world, measurements of volume changes in organs and/or body parts as a result of their blood flows are known under the term plethysmography.

Methods for determining the blood flow of the gastrointestinal tract are known per se, namely: indocyanine green clearing, stomach tonometry, videoscopy of the tongue blood flow and determination of the oxygen saturation of the large intestine. The most significant disadvantage of these methods is that they are either indirect methods in which the final result is only obtained after some time in the laboratory, or experimental methods, which have not yet been validated. Additionally, the reliability of these methods is not very high, certainly where it concerns determinations in or at body parts and/or organs of which the direct relation to the gastrointestinal tract is not convincing.

However, in severe situations, it is of great importance to be able to know immediately how the blood flow of the gastrointestinal tract is. Here, one can think of e.g. patients being in shock, by whatever cause. In case of a shock, there is a redistribution of the blood flow to the vital organs such as the brain, heart and muscles, causing a reduced blood flow in other organs, including the gastrointestinal tract. If such a situation lasts too long, this can cause a significant deterioration in the function of the gastrointestinal tract, which may lead to a further deterioration in the general physical condition of the patient. The described process can go very quickly and may result in death of the patient. The process can be influenced by medicaments, in which, however, it is of great importance that the effect(s) of said medicaments can be determined immediately.

Apart from the shock condition, in many other situations too it could be very important to be able to monitor the blood flow of the gastrointestinal tract in real time. Here, one can think of an operating room and Intensive Care, where the blood flow of the gastrointestinal tract can be immediately compared to the heart performance (cardiac output) and the treating physician can act directly and adequately on the basis of those data.

SUMMARY OF THE INVENTION

In order to allow for realization of such immediate determination of the blood flow of the gastrointestinal tract, the invention provides for a measuring member, comprising an intestinal probe being provided with a supporting body at or near its distal end, with at least one pressure sensor mounted on the supporting body. According to a further development, it is preferably provided that the supporting body is an inflatable flexible body.

In most cases, the intestinal probe having the measuring member is positioned into the intestine through the oral cavity with a gastroduodenojejunoscope, which is in the standard equipment of a gastroenterologist. The supporting body with the pressure sensor mounted thereon will abut the intestinal wall, which in case of an inflatable flexible body will happen by inflating it. The inflatable flexible body has the advantage that it can be brought under exactly the desired pressure so that the pressure sensor will abut the intestinal wall without squeezing or otherwise affecting the blood flow of the intestinal wall at that location.

The intestinal probe can be a probe which is intended substantially for inserting the measuring member. However, this probe can be designed for simultaneously serving as a nutritional probe. The opposite is also possible, namely, that the measuring member is mounted on a nutritional probe, such as a jejunum probe, as a result of which insertion of the nutritional probe simultaneously provides the possibility of monitoring the blood flow of the gastrointestinal tract. The latter is especially important in case of severely ill patients that must be artificially fed internally and thus need not be additionally loaded unnecessarily.

Further, the measuring member can also be mounted on nutritional probes that are not inserted through the oral cavity, but are positioned in the small intestine directly through the abdominal wall.

Especially with a probe which is also used as a nutritional probe, it is important that when used with an inflatable flexible body, it will not be squeezed on tensioning of the inflatable flexible body. To that end, according to the invention the inflatable flexible body engages the outer side of the intestinal probe and encloses it across part of its length. Further, only the outer circumference of the inflatable body is at least partly flexible, to whit in such a way that no deformation is possible at the location where the inflatable body engages the probe.

It is important that the inflatable body, with the desired pressure, will only abut the intestinal wall where the pressure probe is mounted on the inflatable flexible body. To that end, the inflatable flexible body, seen in longitudinal direction of the intestinal probe, has an approximately elliptical cross-section. Preferably, that the inflatable flexible body has an approximately circular cross-section transverse to the longitudinal direction of the intestinal probe. With such a design, the inflatable flexible body is normally in peripheral contact with the inner side of the intestine. The inflatable flexible body mounts at least one pressure sensor. Thus, the blood flow is hindered in the least possible way by the measuring member abutting the intestinal wall, and the pressure sensor can provide a reliable measurement of pressure differences in the blood flow of the gastrointestinal tract. It is possible to employ several pressure sensors, in which the individual signals can be used to check the reliability of the measurements, among other things.

The pressure applied in the flexible body must therefore not be higher than the average pressure in the discharging blood vessels or the pressure in the abdomenal cavity. Usually, this means that the pressure in the inflatable flexible body will not be higher than about 5 cm $H_2O$.

According to another embodiment, the inflatable flexible body has an approximately elliptical cross-section transverse to the longitudinal direction of the intestinal probe. In this embodiment, the inflatable flexible body normally has two opposite points of contact or tangent planes with the intestinal wall. At least one of these locations mounts a pressure sensor. Thus, the blood flow is hindered in the least possible way by the measuring member abutting the intestinal wall and the pressure sensor can provide a reliable measurement of pressure differences in the blood flow. It is possible to employ two opposite pressure sensors, in which the individual signals can be used for checking the reliability of the measurements.

According to a further development, the inflatable flexible body also serves for establishing and measuring the intestinal peristalsis. By measuring pressure variations in the inflatable flexible body, one can establish immediately whether or not the peristalsis of the intestine is functioning and, if this is the case, what its force and frequency are. Besides the blood flow of the gastrointestinal tract, this is a further important parameter for intestine functioning.

Further, the invention provides for a device intended for cooperation with the measuring member, the device being provided with apparatus for registration of the pressure measured in real time by the pressure sensor and apparatus for reproducing it graphically or otherwise. According to a further development, means apparatus for calculating the blood flow of the gastrointestinal tract from the pressure registered in real time have been provided. This can occur by taking the surface below the curve of the course of the pressure in real time as a measure for the blood flow of the gastrointestinal tract.

Preferably, further devices are provided for comparing the calculated blood flow of the gastrointestinal tract to a predetermined value and/or to a value that can be determined elsewhere in the body through measuring blood pressure. This latter value can be a value calculated directly from a blood pressure measured directly in the heart or one of the major blood vessels.

The device according to the invention is further provided with a device for bringing the inflatable flexible body at to a predetermined pressure. The required instrument, such as an air pump, for example, can be part of the device; however it is also possible to provide a device by which an external instrument can be operated. The device according to the invention further comprises apparatus for real time registration of the pressure in the inflatable flexible body and apparatus for reproducing it graphically or otherwise.

The intestine peristaltis can be carefully monitored through the pressure variations in the inflatable flexible body. Here, signaling apparatus can further be provided for signaling exceeding of threshold values in frequency and pressure.

The intestine peristaltis also provides for a change in the pressure measured with the pressure sensor. However, the frequency of the peristaltis and the frequency of the pressure signal measured with the pressure sensor are so different from one another, that the changes in the measurements of the pressure sensor caused by the peristaltis can be simply filtered out by software. The apparatus for doing this are also part of the device.

BRIEF DESCRIPTION OF THE FIGURES

The invention is further explained by way of the example given in the drawing, in which.

DETAILED DESCRIPTION

Figure 1:
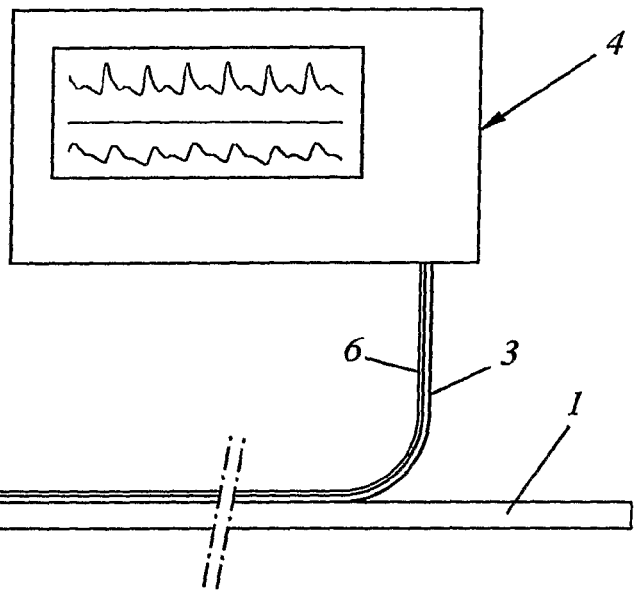
FIG. 1 illustrates schematically a probe with the measuring member and the device to which the measuring member is connected.

FIG. 1 shows schematically an illustration of an intestinal probe 1 to which an inflatable flexible body 2 is mounted at or near its distal end. An air line 3, intended for inflating the inflatable flexible body, extends from the inflatable flexible body past the intestinal probe to a device 4. The air line 3 is coupled to an air pump not further indicated in the drawing, which can be an air pump incorporated in the device 4 or an external air pump being driven from the device 4. At the same time, the air line 3 and the inflatable flexible body 2 are used together for registration of any occurrence of pressure changes in the inflatable flexible body 2 as a consequence of the intestine peristaltic or the lack of it.

Figure 2:
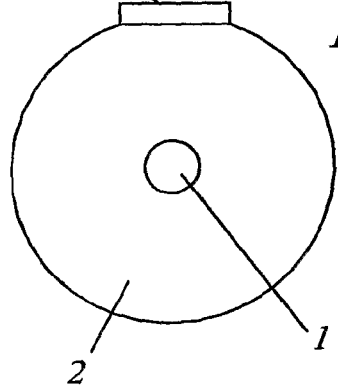
FIG. 2 illustrates a cross-section on an enlarged scale, of the measuring member and the probe.

A pressure sensor 5 is mounted on the inflatable body 2 and is connected to the device 4 through a connection 6. Preferably, the pressure sensor 5 is an electronic sensor that produces an electric signal corresponding to the pressure or the pressure changes. The flexible inflatable body 2 is elliptical in longitudinal direction and has a circular cross-section in the direction transverse to it (see also FIG. 2), so that the pressure sensor 5 will abut the intestinal wall with certainty when the measuring member is inserted in the intestine. Further, the inflatable flexible body 2 is formed in such a way, that it is not deformable at the location of engagement with the intestinal probe 1 or the fixed connection with it, so that the intestinal probe 1 can not be squeezed. Therefore, the intestinal probe 1 can at the same time continue being used as nutritional probe.

Figure 3:
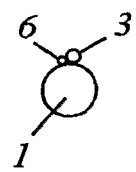
FIG. 3 illustrates a cross-section on an enlarged scale, of the probe.

FIG. 3 shows the cross-section of the intestinal probe 1 having the air line 3 of the inflatable flexible body 2 and the connection 6 of the pressure sensor 5 mounted on it. Air line 3 and connection 6 can be fixedly connected to the intestinal probe 1 by e.g. glueing or otherwise adhering it, or by mounting intestinal probe 1, air line 3 and connection 6 within a tight-fitting and sealing outer enclosure.

Figure 4:
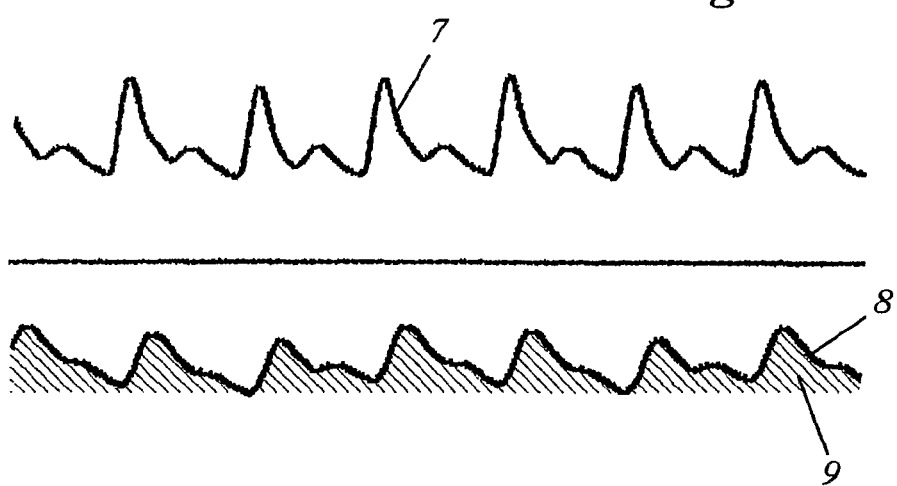
FIG. 4 illustrates two curves of a blood pressure measured directly and a pressure measured using a plethysmograph.

FIG. 4 shows an example of a graphical image that can be obtained on device 4, of e.g. a blood pressure 7 measured through a tube in an artery and a pressure 8 measured with a plethysmograph, which could be e.g. a pressure sensor 5 located against the intestinal wall. The surface below the measured pressure curve represents a measure for the blood flow, which is indicated by shading 9 for the curve 8. Shading 9 extends across the entire illustrated curve 8 in the drawing, but this measure for the blood flow can be taken in any desired time interval. Depending on the measuring method and the location where the measurement is carried out, it may be necessary to apply a correction factor for being able to calculate the actual blood flow from the measured progress of pressure. Such a correction factor can be applied to the measurement data by software.

The invention claimed is:

1. A system for measuring the blood flow of a gastrointestinal tract, comprising
   (a) an elongated probe having a distal region, the probe configured for placement within the intestine;
   (b) an inflatable body disposed on the distal region;
   (c) a sensor operatively associated with the inflatable body, the sensor configured to generate a plethysmographic signal corresponding to time-wise changes in blood flow volume within the intestine; and
   (d) a device configured to control inflation of the inflatable body to a condition wherein the inflatable body and the sensor abut against a wall surface of the intestine without affecting blood flow within the intestine, the device configured to process the plethysmographic signal to generate a signal corresponding to at least one of the blood pressure and intestinal peristalsis at the location of the sensor within the intestine.

2. The system of claim 1, wherein the sensor is mounted on an outer circumference of the inflatable body.

3. The system of claim 1, wherein the device is configured to filter the plethysmographic signal to derive a signal corresponding to intestinal peristalsis.

4. The system of claim 1, wherein the device is configured to control inflation of the inflatable body to a predetermined pressure.

5. The system of claim 1, wherein the device includes a graphical display, and the plethysmographic signal is displayed on graphical display.

6. The system of claim 3, wherein the device is configured to compare the signal corresponding to intestinal peristalsis threshold value.

7. The system of claim 1, wherein said inflatable body has an elliptical cross-sectional configuration.

8. The system of claim 1, wherein the elongated probe is configured for positioning within the intestine through an oral cavity.

9. The system of claim 1 wherein the elongated probe is configured for positioning within the intestine through the abdominal wall.

10. The system of claim 1 wherein the elongated probe is configured to function as a nutritional probe.

11. A system for monitoring blood flow of a gastrointestinal tract, comprising
   an elongated probe having a proximal end and a distal region, the probe configured for placement within the intestine;
   an inflatable body disposed on the distal region, the inflatable body communicating with the proximal end of the probe;
   an electronic sensor operatively associated with the inflatable body, the electronic sensor configured to generate a plethysmographic signal corresponding to time-wise changes in blood flow volume within the intestine; and
   a monitor operatively coupled to the inflatable body and the electronic sensor, the monitor configured to control inflation of the inflatable body to a condition so that the electronic sensor abuts against a wall surface of the intestine without diminishing blood flow therein, the monitor configured to process the plethysmographic signal to generate a signal corresponding to at least one of the blood pressure and intestinal peristalsis at the location of the electronic sensor.

12. The system of claim 11, wherein the electronic sensor is mounted on an outer circumference of the inflatable body.

13. The system of 11, wherein the device is configured to filter the plethysmographic signal to derive a signal corresponding to intestinal peristalsis within the intestine at the location of the electronic sensor.

14. The system of claim 11, wherein the monitor is configured to control inflation of the inflatable body to a predetermined pressure.

15. The system of claim 11, wherein the monitor includes a graphical display, and the plethysmographic signal is displayed on graphical display.

16. The system of claim 13, wherein the monitor is configured to compare the signal corresponding to intestinal peristalsis with a threshold value.

17. The system of claim 11, wherein said inflatable body has an elliptical cross-sectional configuration.

18. The system of claim 11, wherein the elongated probe is configured for positioning within the intestine through an oral cavity.

19. The system of claim 11 wherein the elongated probe is configured for positioning within the intestine through the abdominal wall.

20. The system of claim 11 wherein the elongated probe is configured to function as a nutritional probe.

* * * * *